United States Patent [19]
Detmar et al.

[11] 3,930,402
[45] Jan. 6, 1976

[54] VISCOSIMETER

[75] Inventors: Dirk Adrianus Detmar, Rijswijk Zh; Jan Van der Sluis, Delft; Izak Johannes Stolk, Delft; Marius Hendrik Johan Zuidweg, Delft, all of Netherlands

[73] Assignee: Gist-Brocades N.V., Delft, Netherlands

[22] Filed: Feb. 27, 1974

[21] Appl. No.: 446,261

[30] Foreign Application Priority Data
Mar. 2, 1973 Netherlands.................... 7302934

[52] U.S. Cl. .................................................. 73/55
[51] Int. Cl.² ........................................ G01N 11/04
[58] Field of Search........................ 73/55, 406, 438

[56] References Cited
UNITED STATES PATENTS

| | | | |
|---|---|---|---|
| 3,327,522 | 6/1967 | Hoyt...................................... | 73/55 |
| 3,548,638 | 12/1970 | Uchida et al. ......................... | 73/55 |
| 3,610,026 | 10/1971 | Topham................................ | 73/55 |
| 3,802,265 | 4/1974 | Wood................................... | 73/406 X |
| 3,808,877 | 5/1974 | Blair..................................... | 73/55 |

Primary Examiner—Richard C. Queisser
Assistant Examiner—Joseph W. Roskos
Attorney, Agent, or Firm—Fleit & Jacobson

[57] ABSTRACT

Viscosimeter comprising a flow system for the liquid to be tested, having a narrow zone, zones for determining the pressure of the liquid to be tested located before and after the narrow zone, said zones for determining the pressure of the liquid to be tested being surrounded by tubes of a thin-walled material adapted to transfer the pressure of the liquid within the tubes to pressure transduction liquids outside each of the tubes, each of said pressure transduction liquids being in contact with one of two pressure chambers of a pressure difference recording means in such a manner that the pressures of the liquid to be tested at both sides of the narrow zone are transferred to said pressure chambers.

9 Claims, 4 Drawing Figures

VISCOSIMETER

BACKGROUND OF THE INVENTION

Viscosimeters are generally known, for example, the Ostwald viscosimeter (Glasstone, Textbook of Physical Chemistry, 2nd Ed., 10th Printing (1954) D. vam Nostrand Co., page 498), comprising a capillary adapted to the flow of the liquid to be determined. Such a viscosimeter is adapted only to measurements on liquids having a constant viscosity and it cannot be used for measurements of liquids having a varying viscosity, e.g. due to a reaction in the liquid, such as an enzymatically decomposing starch or protein solution having a decreasing viscosity, a polymerizing solution having an increasing viscosity, or a DNA solution in which the viscosity varies due to influences of temperature, pH or ion concentration.

The generally known method of the falling ball (Glasstone, loc. cit. page 498 and 499) is not suitable for this purpose either.

It is an object of the invention to provide a low feed, fast response, very low time of delay viscosimeter which, in particular, is suitable for continuous measurements of liquids showing a viscosity varying with the time.

Thus, the invention provides a viscosimeter comprising a flow system for the liquid to be tested, having a narrow zone, zones for determining the pressure of the liquid to be tested located before and after the said narrow zone, said zones for determining the pressure of the liquid to be tested being surrounded by tubes of a thin-walled material adapted to transfer the pressure of the liquid within the tubes to pressure transduction liquids outside each of the tubes, each of said pressure transduction liquids being in contact with one of two pressure chambers of a pressure difference recording means in such a manner that the pressures of the liquid to be tested at both sides of the narrow zone are transferred to said pressure chambers.

The tubes of thin-walled material are within chambers containing the pressure transduction liquid, said chambers being connected to connecting tubes, each of them leading one of the two pressure chambers of the pressure difference recording means.

The viscosimeter according to the invention enables in an easy manner to follow continuously the viscosity of a liquid flowing through the narrow zone, preferably a capillary, at constant speed.

The relationship between the viscosity and the pressure gradient over a capillary may be derived from the Hagen-Poiseuille equation for a liquid flowing through a capillary:

$$\eta = \frac{\pi R^4}{8V} \frac{P_1 - P_2}{L} t \qquad (1)$$

in which
$\eta$ = viscosity of the liquid
$R$ = radius of the cross-section of the capillary
$V$ = volume of the liquid flowing through the capillary within a period $t$
$P_1 - P_2$ = pressure difference of the liquids at both sides of the capillary
$L$ = length of the capillary From this equation, which is a good approximation when a laminary flow is maintained in the capillary, it may easily be concluded that, at constant flow speed, the viscosity is proportional to the pressure difference, and that variations in viscosity thus are indicated by the variations of the pressure difference which may be transferred, for example, into an electrical signal by means of a device acting according to the inductive, capacitive or piezoelectrical principle, which signal may be made visible by a recorder.

An advantage of the application of an additional liquid located between the spaces with the zones surrounded by the thin-walled, pressure-transferring material and the pressure difference meter, is that the liquid to be determined cannot remain in dead spaces and influence the measurement wrongly in this manner.

When, for example, quick changes occur in the viscosity of the liquid to be determined, the liquid present in the connecting tubes and diffusing into the liquid to be tested, would give rise to false measurements, and this may be avoided by the device of the invention.

Since the viscosity is generally highly dependent on the temperature, the capillary of the viscosimeter according to the invention is preferably provided with a jacket through which thermostatted liquid may be passed. It is also possible to place the whole viscosimeter in a thermostatted zone. Further, the liquid to be tested is preferably heated to the desired temperature by means of a thermostat before it is carried through the viscosimeter according to the invention.

The above-mentioned thin-walled, pressure-transferring material is preferably a flexible thin-walled rubber which is very useful for viscosity measurements in aqueous media. Another suitable material is, for example, polyvinylalcohol, enabling measurements is several organic solvents.

According to a preferred embodiment, the ends of the capillary are funnel-shaped and the zones surrounded by the tubes of thin-walled material are located in line with the capillary. Thus, the capillary may easily be cleaned by, e.g. mechanical means, without the necessity of demounting the apparatus.

It is appreciated that the viscosimeter according to the invention may also be used for measurements of the absolute viscosity; in that case, the viscosimeter has to be calibrated by means of two or more liquids having a known viscosity.

DETAILED DESCRIPTION OF THE DRAWINGS

Figure 1:
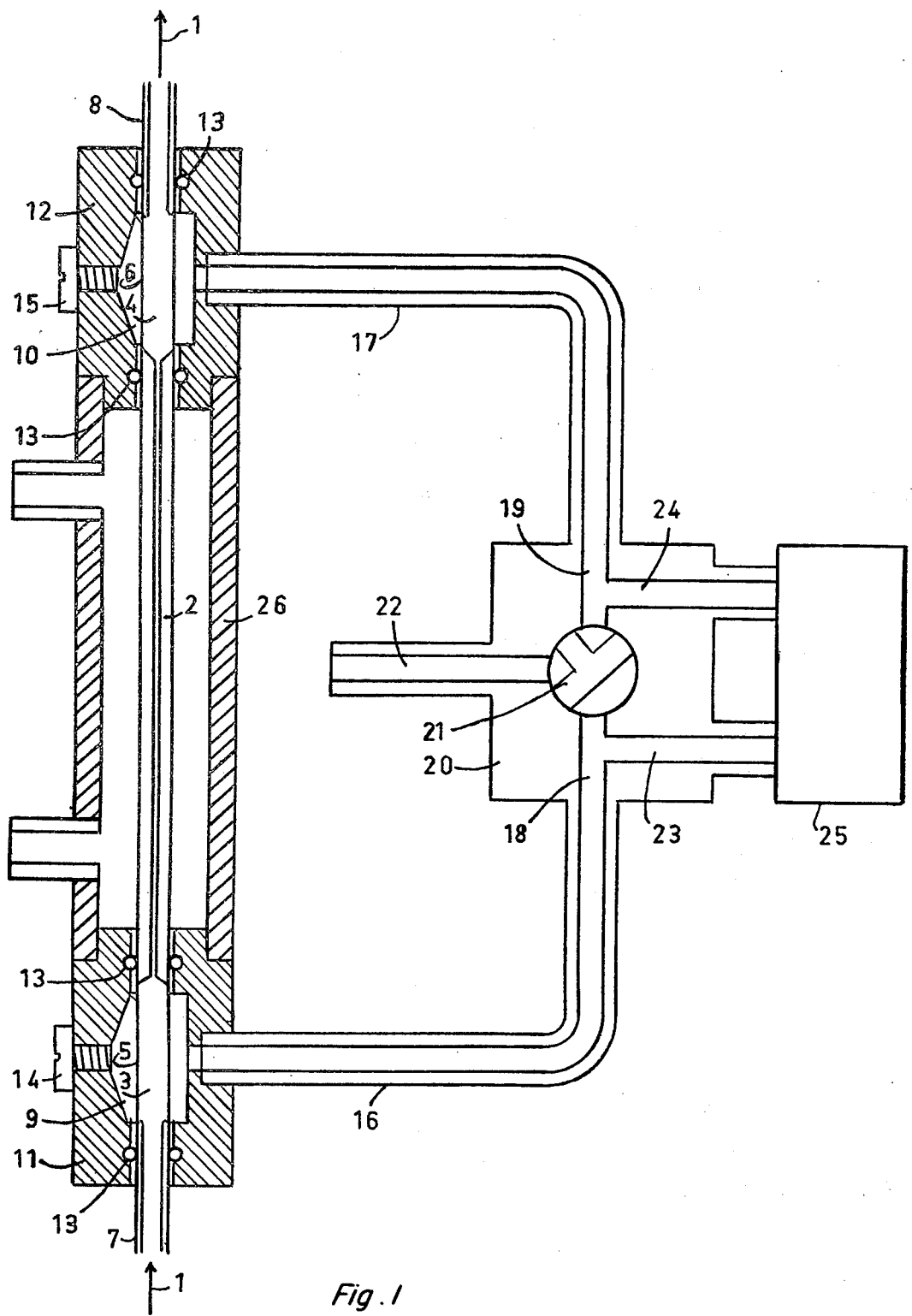
FIG. 1 shows a section through a preferred embodiment of the device according to the invention.

The device shown in FIG. 1 comprises a flow system for the liquid to be tested, indicated by arrows 1. The flow system comprises a capillary 2, preceded by a zone 3 and followed by a zone 4, each of which being surrounded by a flexible thin-walled rubber tube 5 and 6, respectively. One end of each of the tubes 5 and 6 is placed over an end of the capillary 2, whereas the other ends of the tubes are placed over an inlet and outlet tubes 7 and 8, respectively, for the liquid to be tested. The zones 3 and 4 with the rubber tubes 5 and 6 are surrounded by chambers 9 and 10 defined by containers 11 and 12 in which the capillary 2 and the inlet and outlet tubes 7 and 8 are fixed by rubber rings fixing also the rubber tubes 5 and 6. The chambers 9 and 10 can be reached through openings which may be closed by screws 14 and 15. The chambers 9 and 10 are further connected to the channels 18 and 19 of a connecting piece 20 by by means of connecting tubes 16 and 17. The connecting piece is provided with a three way valve 21 allowing a mutual connection of the channels 18 and 19 and a channel 22. The channel 22 is connected to a supply vessel (not indicated). The channels 18 and 19 are further connected to branch channels 23 and 24, respectively, which in turn are connected to a pressure transducer. The pressure transducer is connected to a recorder.

The combination of the pressure transducer and the recorder is schematically indicated in the drawing by a block 25. The pressure transducer operates as follows: The liquids, between which the pressure difference is to be measured, occupy each a separate chamber. The chambers are separated by a corrosion-free steel membrane deflecting upon the occurrence of a variation of pressure difference. The membrane is located in a magnetic field originated by two coils in a bridge. When the membrane deflects, the change of the selfinductions of the coils will cause an unbalance of the bridge and give rise to an output signal which, after sufficient amplification, may be supplied to, for example, a recorder, so that the pressure changes may be recorded continuously.

Capillary 2 is surrounded by a jacket 26 adapted to be passed by a medium from a thermostat bath.

The flexible rubber tubes 5 and 6 may be sufficiently flexible and thin-walled as to enable a clear recording of pressure changes. A suitable method for the preparation of the flexible rubber tubes is the following: a stirring rod having a cross-section equal to the external cross-section of the capillary is submerged three times in a rubber latex and dried every time in air. By means of talc powder, the flexible rubber tube thus obtained is stripped off from the stirring rod.

Before use, the chambers 9 and 10, the connecting tubes 16 and 17 connected therewith, and the channels 18, 19, 23 and 24 have to be filled with a liquid adapted to transfer pressure changes to the transducer. Therefore, the device is held horizontally (i.e. the tubes 16 and 17 horizontal, and the block 20 below), the screws 14 and 15 are unscrewed and the three way valve 21 is adjusted so that the channels 18, 19 and 22 are mutually connected.

Liquid from the supply vessel, for example distilled water, is permitted to enter, allowing the air present to escape through the openings of the screws 14 and 15 until the whole cavity is filled and the chambers 9 and 10 run over. The three way valve 21 is turned one eighth of a revolution, disconnecting the mutual connection between the channels 18, 19 and 22, and the screws 14 and 15 are screwed tight. For measurements, the device is placed vertically (i.e. in such a manner that the capillary is in a vertical position and the liquid to be tested is allowed to flow upwards) in order to avoid settling of air bubbles anywhere.

Figure 2:
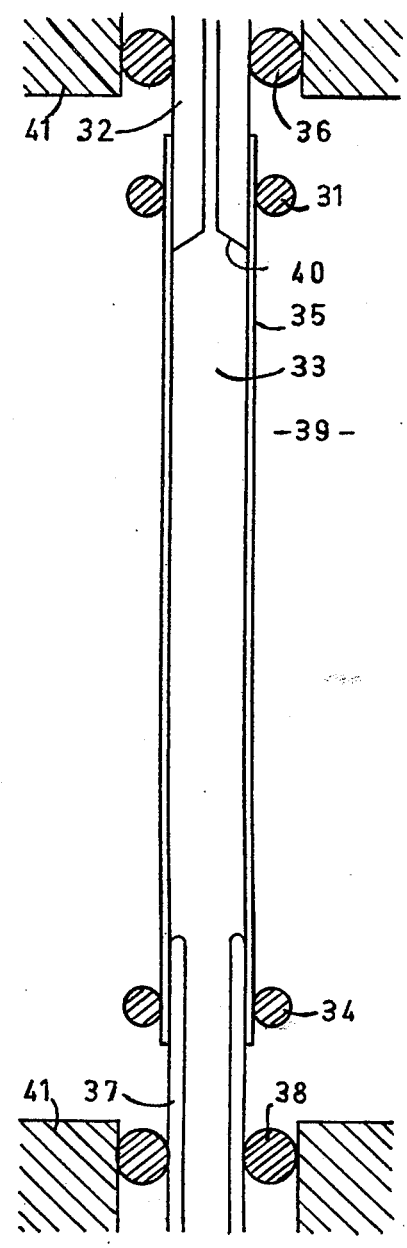
FIG. 2 shows a section through one of the chambers of another embodiment of the device according to the invention.

FIG. 2 shows a part of another embodiment of the device according to the invention. This embodiment comprises also a capillary 32, from which only the lower part, ending in a zone 33, is shown. The zone 33 is surrounded by a flexible, thin-walled, pressure-transferring tube 35 which, in turn, is surrounded by a chamber 39. One end of the flexible tube 35 is placed over the capillary and is held in its position by an O-ring 31. The other end of the flexible tube 35 is placed over an inlet tube 37, and is held by an O-ring 34. The capillary is held in its position by an O-ring 36 in a holder 41. The inlet tube 37 is held by an O-ring 38 in the holder 41. This construction has the advantage that it is demounted easily and thus, can be cleaned easily. Also the funnel-shaped end of the capillary, indicated in FIG. 2 by a reference 40, contributes to easy cleaning thereof.

Figure 3:
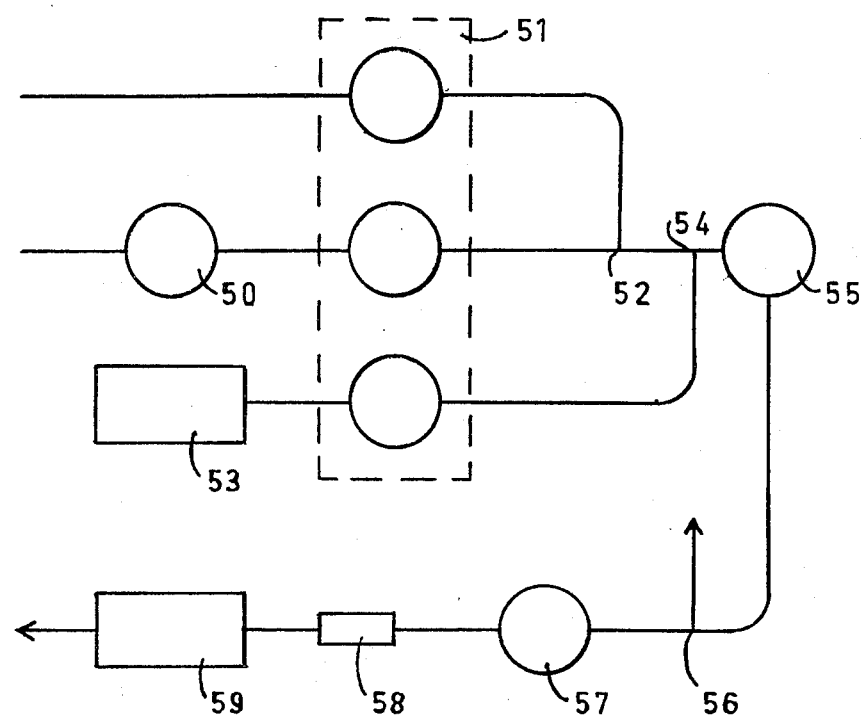
FIG. 3 is a schematic view of an arrangement including the viscosimeter according to the invention.

The device of FIGS. 1 or 2 can be introduced in an arrangement as described and indicated in FIG. 3. From a supply vessel, a substrate solution, for example a starch solution, is pumped to a heating coil 50, placed in a thermostat of 40°C, by means of a peristaltic pump 51. By means of the peristaltic pump 51, air is introduced which, through a T-piece 52, is added to the substrate solution, so that the liquid is segmented. From a sampler 53, which alternatively supplies a sample solution, for example, an amylase solution, and water, the peristaltic pump 51 pumps the sample which, through a T-piece 54, is added to the substrate solution. The segmented reaction mixture proceeds along an incubation coil 55, also placed in a thermostat of 40°C. Then, the reaction mixture passes a T-piece 56 allowing excess of reaction mixture and air to escape. Thereafter, the reaction mixture passes a peristaltic pump 57 of a low pulse dosing the reaction mixture at the desired speed to the viscosimeter indicated by reference number 59 through a pulse depressor 58 consisting of a tightly closed vessel in which an air cushion is present above the liquid. The viscosimeter is connected to a pressure transducer (not indicated) which, in turn, is connected to a recorder. The combination of flexible tubes and peristaltic pump is adjusted in such manner that, for example, the substrate solution is pumped with a rate of 4.0 ml/minute, while the air is pumped with a rate of 1.0 ml/minute, and the enzyme sample with a rate of 0.4 ml/minute. The sampler is arranged so that it supplies alternatively sample solution and water during periods of 1½ minutes each. The incubation time during which the enzyme reacts with the substrate can be varied, for example, by adjusting the length of the incubation coil 55.

Figure 4:
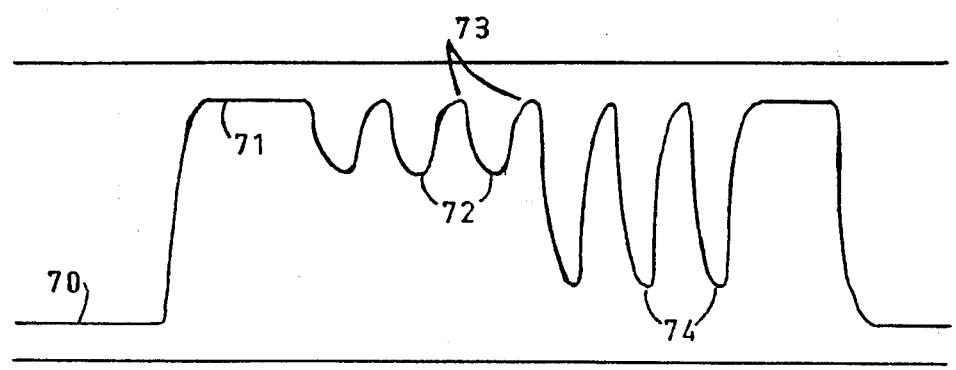
FIG. 4 shows the result of the measurement carried out by means of the arrangement according to FIG. 3.

The result of an experiment carried out under the abovementioned circumstances is schematically indicated in FIG. 4, in which, on a decreased scale, a graph is shown, as it leaves the recorder. The part 70 is the deflection, obtained by flowing water through the system; the part 71 corresponds to the deflection of the substrate solution with water; the deflections 72 correspond to the substrate solution to which a certain amount of enzyme is added, the deflections 73 correspond to the substrate solution with water again; and the deflections 74 correspond to the substrate solution to which a larger amount of enzyme is added.

In a similar manner, analoguous curves are obtained with other enzymes using other substrates, i.a. with a proteolytic enzyme and casein.

It should be appreciated that the invention is not restricted to the embodiments shown, but that many alterations and modifications may be made by those skilled in the art without departing from the spirit and scope of the invention as defined in the claims.

What we claim is:

1. A viscosimeter for testing liquids comprising: a flow system for liquid to be tested, having a capillary; zones for determining the pressure of the liquid to be tested located before and after the capillary, said zones for determining the pressure of the liquid to be tested being surrounded by tubes of a thin-walled material adapted to transfer the pressure of the liquid within the tubes to pressure transduction liquids outside each of the tubes; a pressure difference recording means having two chambers, each of said pressure transduction liquids being in contact with one of said two pressure chambers of said pressure difference recording means in such a manner that the pressure of the liquid to be tested at both sides of the capillary are transferred to said pressure chambers.

2. Viscosimeter according to claim 1, wherein the tubes of thin-walled material are flexible, thin-walled rubber tubes.

3. Viscosimeter according to claim 2, wherein the capillary is provided with a jacket through which a thermostatted liquid may be passed.

4. Viscosimeter according to claim 1, wherein the ends of the capillary are funnel-shaped and wherein the zones for determining the pressure of the liquid to be tested are located in line with the capillary.

5. Viscosimeter according to claim 1, wherein the tubes of thin-walled material are within chambers containing the pressure transduction liquid, said chambers being connected to connecting tubes, each of them leading to one of the two pressure chambers of the pressure difference recording means.

6. A viscosimeter comprising:
   a housing;
   a capillary tube positioned axially within said housing through which test fluid to be analyzed flows;
   means for measuring the pressure drop of said test fluid flowing through said capillary tube comprising first and second spaced apart pressure sensing zones positioned in said housing, one zone being attached to each end of said capillary tube, each pressure sensing zone having a container housing defining a chamber therein and a thin walled tube surrounding said pressure sensing zone so that test fluid flowing in said capillary tube flows through said pressure sensing zone and exerts pressure on said thin walled tube;
   means for sensing pressure in said pressure sensing zones comprising a differential pressure transducer;
   pressure transduction tubes connecting said differential pressure transducer to each of said pressure sensing zones and pressure transduction liquid which completely fills said transduction tubes and said pressure sensing zones and is separated from said test fluid flowing by said thin-walled tubes, said thin walled tubes transferring pressure from said pressure sensing zones to said differential pressure transducer via said pressure transduction liquid; and
   means for recording the differential pressure sensed by said differential pressure transducer.

7. A measuring circuit for determining liquid pressure comprising:
   a viscosimeter comprising:
   a housing;
   a capillary tube positioned axially within said housing through which test fluid to be analyzed flows;
   means for measuring the pressure drop of said test fluid flowing through said capillary tube comprising first and second spaced apart pressure sensing zones positioned in said housing, one zone being attached to each end of said capillary tube, each pressure sensing zone having a container housing defining a chamber therein and a thin walled tube surrounding said pressure sensing zone so that test fluid flowing in said capillary tube flows through said pressure sensing zone and exerts pressure on said thin walled tube;
   means for sensing pressure in said pressure sensing zones comprising a differential pressure transducer, pressure transduction tubes connecting said differential pressure transducer to each of said pressure sensing zones, and pressure transduction liquid which completely fills said transduction tubes and said pressure sensing zones and is separated from said test fluid flowing by said thin walled tubes, said thin walled tubes transferring pressure from said pressure sensing zones to said differential pressure transducer via said pressure transduction liquid;
   means for recording the differential pressure sensed by said differential pressure transducer; and
   a supply of liquid to be tested.

8. Measuring circuit according to claim 7, wherein the supply for the liquid to be tested consists of a zone in which the temperature of substrate may be brought to a desired level, a zone adapted to receive a reagent in a predetermined amount, and a zone in which the thus obtained liquid to be tested is supplied to the viscosimeter.

9. Viscosimeter comprising a flow system for the liquid to be tested, having a narrow zone, zones for determining the pressure of the liquid to be tested located before and after the said narrow zone, said zones for determining the pressure of the liquid to be tested being surrounded by tubes of a thinwalled material adapted to transfer the pressure of the liquid within the tubes to pressure transduction liquids outside each of the tubes, said tubes being within chambers containing the pressure transduction liquid, said chambers being connected to connecting tubes, a three way valve which may be brought in such a position that the connecting tubes are in mutual contact prior to filling the device with the pressure transduction liquid, said valve also allowing to form a connection with a supply vessel for the pressure transduction liquid, each of said pressure transduction liquids being in contact with one of two pressure chambers of a pressure difference recording means in such a manner that the pressures of the liquid to be tested at both sides of the narrow zone are transferred to said pressure chambers.

* * * * *